United States Patent
Kobayashi et al.

(10) Patent No.: US 7,635,186 B2
(45) Date of Patent: Dec. 22, 2009

(54) OPHTHALMOLOGIC MEASURING APPARATUS

(75) Inventors: Mariko Kobayashi, Tokyo (JP); Tatsuo Yamaguchi, Tokyo (JP); Toshifumi Mihashi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 268 days.

(21) Appl. No.: 11/681,420

(22) Filed: Mar. 2, 2007

(65) Prior Publication Data

US 2007/0216866 A1 Sep. 20, 2007

(30) Foreign Application Priority Data

Mar. 20, 2006 (JP) ............... 2006-076712

(51) Int. Cl.
*A61B 3/10* (2006.01)

(52) U.S. Cl. ............... 351/221; 351/215; 351/205

(58) Field of Classification Search ............... 351/221
See application file for complete search history.

(56) References Cited

U.S. PATENT DOCUMENTS

| | | | | |
|---|---|---|---|---|
| 6,027,216 | A * | 2/2000 | Guyton et al. | 351/200 |
| 6,155,684 | A * | 12/2000 | Bille et al. | 351/212 |
| 6,379,005 | B1 * | 4/2002 | Williams et al. | 351/211 |
| 6,827,442 | B2 * | 12/2004 | Ross et al. | 351/205 |
| 7,249,852 | B2 * | 7/2007 | Mihashi et al. | 351/221 |
| 7,364,296 | B2 * | 4/2008 | Miller et al. | 351/206 |
| 2005/0099599 | A1 * | 5/2005 | Mihashi et al. | 351/205 |

FOREIGN PATENT DOCUMENTS

| | | |
|---|---|---|
| JP | 11-137520 A | 5/1999 |
| JP | 2004-500195 | 1/2004 |
| JP | 2004-81725 A | 3/2004 |
| JP | 2005-506107 | 3/2005 |
| JP | 2005-275305 A | 10/2005 |
| WO | WO 01/58339 A3 | 8/2001 |
| WO | WO 02/075367 A3 | 9/2002 |

OTHER PUBLICATIONS

Machine translation of JP 2004-081725.*

* cited by examiner

*Primary Examiner*—Jessica T Stultz
(74) *Attorney, Agent, or Firm*—Foley & Lardner LLP

(57) ABSTRACT

There is provided a Shack-Hartmann wavefront sensor which can repetitively perform a measurement at high speed and at short measurement intervals. An illuminating optical system includes a first polarizing optical member to alternately change a polarization condition to a first polarized light or a second polarized light, and illuminates a pulse light from a laser light source part to an ocular fundus of a subject eye through a first polarizing optical member. A light receiving optical system includes a second polarizing optical member to select each polarized light component of the reflected light from the subject eye illuminated according to the polarization condition of the first polarizing optical member, and a first and a second light receiving parts to alternately receive the reflected light of the selected polarized light component. An ophthalmologic measuring apparatus measures the wavefront aberration of the subject eye at short intervals based on the output of the first and the second light receiving parts.

8 Claims, 12 Drawing Sheets

TIME CHART WHEN TWO CCDS ARE USED $$\begin{bmatrix}
i & 2j-i & \\
0 & 0 & 1 \\
1 & -1 & r\sin(t) \\
1 & 1 & \cos(t)\,r \\
2 & -2 & r^2\sin(2t) \\
2 & 0 & 2r^2-1 \\
2 & 2 & r^2\cos(2t) \\
3 & -3 & r^3\sin(3t) \\
3 & -1 & (3r^3-2r)\sin(t) \\
3 & 1 & (3r^3-2r)\cos(t) \\
3 & 3 & r^3\cos(3t) \\
4 & -4 & r^4\sin(4t) \\
4 & -2 & (4r^4-3r^2)\sin(2t) \\
4 & 0 & 6r^4-6r^2+1 \\
4 & 2 & (4r^4-3r^2)\cos(2t) \\
4 & 4 & r^4\cos(4t) \\
5 & -5 & r^5\sin(5t) \\
5 & -3 & (5r^5-4r^3)\sin(3t) \\
5 & -1 & (10r^5-12r^3+3r)\sin(t) \\
5 & 1 & (10r^5-12r^3+3r)\cos(t) \\
5 & 3 & (5r^5-4r^3)\cos(3t) \\
5 & 5 & r^5\cos(5t) \\
6 & -6 & r^6\sin(6t) \\
6 & -4 & (6r^6-5r^4)\sin(4t) \\
6 & -2 & (15r^6-20r^4+6r^2)\sin(2t) \\
6 & 0 & 20r^6-30r^4+12r^2-1 \\
6 & 2 & (15r^6-20r^4+6r^2)\cos(2t) \\
6 & 4 & (6r^6-5r^4)\cos(4t) \\
6 & 6 & r^6\cos(6t)
\end{bmatrix}$$

FIG. 9

$$\begin{array}{cc}
i & 2j-i \\
\end{array}$$

$$\begin{bmatrix}
0 & 0 & 1 \\
1 & -1 & y \\
1 & 1 & x \\
2 & -2 & 2yx \\
2 & 0 & 2x^2+2y^2-1 \\
2 & 2 & x^2-y^2 \\
3 & -3 & 3yx^2-y^3 \\
3 & -1 & 3yx^2+3y^3-2y \\
3 & 1 & 3x^3+3xy^2-2x \\
3 & 3 & x^3-3xy^2 \\
4 & -4 & 4yx^3-4y^3x \\
4 & -2 & 8yx^3+8y^3x-6yx \\
4 & 0 & 6x^4+12x^2y^2+6y^4-6x^2-6y^2+1 \\
4 & 2 & 4x^4-4y^4-3x^2+3y^2 \\
4 & 4 & x^4-6x^2y^2+y^4 \\
5 & -5 & 5yx^4-10y^3x^2+y^5 \\
5 & -3 & 15yx^4+10y^3x^2-5y^5-12yx^2+4y^3 \\
5 & -1 & 10yx^4+20y^3x^2+10y^5-12yx^2-12y^3+3y \\
5 & 1 & 10x^5+20x^3y^2+10xy^4-12x^3-12xy^2+3x \\
5 & 3 & 5x^5-10x^3y^2-15xy^4-4x^3+12xy^2 \\
5 & 5 & x^5-10x^3y^2+5xy^4 \\
6 & -6 & 6yx^5-20y^3x^3+6y^5x \\
6 & -4 & 24yx^5-24y^5x-20yx^3+20y^3x \\
6 & -2 & 30yx^5+60y^3x^3+30y^5x-40yx^3-40y^3x+12yx \\
6 & 0 & 20x^6+60x^4y^2+60x^2y^4+20y^6-30x^4-60x^2y^2-30y^4+12x^2+12y^2-1 \\
6 & 2 & 15x^6+15x^4y^2-15x^2y^4-15y^6-20x^4+20y^4+6x^2-6y^2 \\
6 & 4 & 6x^6-30x^4y^2-30x^2y^4+6y^6-5x^4+30x^2y^2-5y^4 \\
6 & 6 & x^6-15x^4y^2+15x^2y^4-y^6 \\
\end{bmatrix}$$

FIG. 10

FIG. 11B  CALIBRATED POINT IMAGES
FIG. 11A  POINT IMAGES OBTAINED WHEN STIGMATIC MODEL EYE IS MEASURED WITH CCD2 OR CCD3

OPHTHALMOLOGIC MEASURING APPARATUS

BACKGROUND OF THE INVENTION

1. Field of the Invention

The present invention relates to an ophthalmologic measuring apparatus, and particularly to an ophthalmologic measuring apparatus which can repeatedly perform a wavefront aberration measurement in a short time.

2. Background Art

Patent documents 1 and 2 disclose an ophthalmologic optical apparatus which measures a wavefront aberration of an eye by using two Shack-Hartmann wavefront sensors.

In patent document 1, in FIG. 12 thereof, a first light receiving part and a third light receiving part correspond to a Shack-Hartmann wavefront sensor. However, their objects are different such that the first light receiving part receives a reflected light flux from a cornea to measure a cornea shape, and the third light receiving part receives a reflected light flux from a retina to measure optical characteristics.

Patent document 2 discloses a structure in which reflected light from a retina is received by a low sensitivity Shack-Hartmann wavefront sensor and a high sensitivity Shack-Hartmann wavefront sensor. Here, the two Shack-Hartmann wavefront sensors are made different from each other in sensitivity, and high-speed photographing is not intended.

Besides, patent document 3 discloses a high-speed continuous photographing system in which the start point of a dead time of a first camera and the end point of a dead time of a second camera are synchronized, the light emission start point of first light emission is made immediately before the start of the dead time of the first camera, while the light emission start point of second light emission is made within the dead time of the first camera and after the end of the dead time of the second camera.

Patent document 4 discloses a system for measuring an aberration of a three-dimensional structure, which includes a light source to generate plural light beams, an optical imaging system to project the light beams to different positions in an objective optical system, and a wavefront sensor to receive scattered lights from the different positions and to detect the respective wavefronts of the scattered lights.

Further, patent document 5 discloses a dynamic range enlarging technique for a wavefront sensor, in which an aberration analysis from an end to an end of a visual system is made possible by a pre-correction system that is positioned between a projection optical system and an eye and compensates an optical beam incident on the subject eye with respect to the aberration of the eye.

[Paten document 1] JP-A-11-137520
[Paten document 2] JP-A-2004-81725
[Paten document 3] JP-A-2005-275305
[Paten document 4] JP-T-2005-506107
[Paten document 5] JP-T-2004-500195

SUMMARY OF THE INVENTION

The aberration of an eye to be measured is changed by ocular movement. Besides, tear fluid on the cornea is also time changed, and this also causes the change of the aberration. Further, a crystalline lens is adjusted according to a distance when a near or distant object is seen, and the aberration is changed also by this. This change has various frequency components, and they are considered to be approximately 20 Hz. There are some researchers who desire to measure a change of, for example, about 100 Hz. Then, it becomes necessary that the aberration of the eye is measured, for example, 50 or more times per second, and the necessity of the high-speed measurement of the eye has been enhanced.

The Shack-Hartmann wavefront sensor includes, for example, a lenslet array having two-dimensionally arranged lenslets, and a digital CCD of 1000×1000 pixels. In the wavefront aberration measurement using the Shack-Hartmann wavefront sensor, when measurement is performed by the digital CCD of about 1000×1000 pixels with less noise, the measurement can be performed with high precision.

However, in the case of the CCD with the specifications as stated above, it is conceivable that there is a limit in performance that a time for reading the charge stored in the CCD after exposure can not be made very fast. For example, in the case of the digital CCD of about 1000×1000 pixels, at present, the number of times of repeated measurement is about 20 times per second. This is determined by the sum of an exposure time and a read time of image data. In the digital CCD, and further, in the CCD with less noise, it takes about several tens milliseconds to read an image. This can be comparable to the exposure time required by the Shack-Hartmann wavefront sensor.

In view of the above, the invention has an object to provide a Shack-Hartmann wavefront sensor in which a measurement interval is short, and a repeated measurement can be performed at high speed (for example, about 50 frames/sec). Besides, the invention has another object to provide an ophthalmologic measuring apparatus in which two CCDs are used, and when one of them is being exposed to light, the other reads image data, so that the number of times of measurement can be ideally doubled as compared with a case where a repeated measurement is performed by one CCD.

According to an aspect of the present invention, there is provided an ophthalmologic measuring apparatus comprising:

a light source part to emit a high-intensity light flux at a specified timing;

an illuminating optical system to illuminate the light flux from the light source part to an ocular fundus of a subject eye;

a light receiving optical system that selectively guides the reflected light flux from the illuminated ocular fundus of the subject eye to a first and a second light receiving parts alternately through a first and a second conversion members each dividing the light flux into at least 17 light fluxes; and a measurement part to measure a wavefront aberration of the subject eye at short intervals based on output from the first and the second light receiving parts.

According to the invention, there can be provided the Shack-Hartmann wavefront sensor in which the measurement interval is short, and the repeated measurement can be performed at high speed (for example, about 50 frames/sec). Besides, according to the invention, there can be provided the ophthalmologic measuring apparatus in which two CCDs are used, and when one of them is being exposed to light, the other reads image data, so that the number of times of measurement can be ideally doubled as compared with the case where the repeated measurement is performed by one CCD.

BRIEF DESCRIPTION OF THE DRAWINGS

FIG. 9 is a view of Zernike polynomials of (r, t) coordinates.

FIG. 10 is a view of Zernike polynomials of (x, y) coordinates.

FIGS. 11A and 11B are explanatory views concerning the correction of arrangement errors of CCDs of respective Shack-Hartmann wavefront sensors.

DETAILED DESCRIPTION OF THE INVENTION

1. Apparatus Structure 1.1 Optical System

Figure 1:
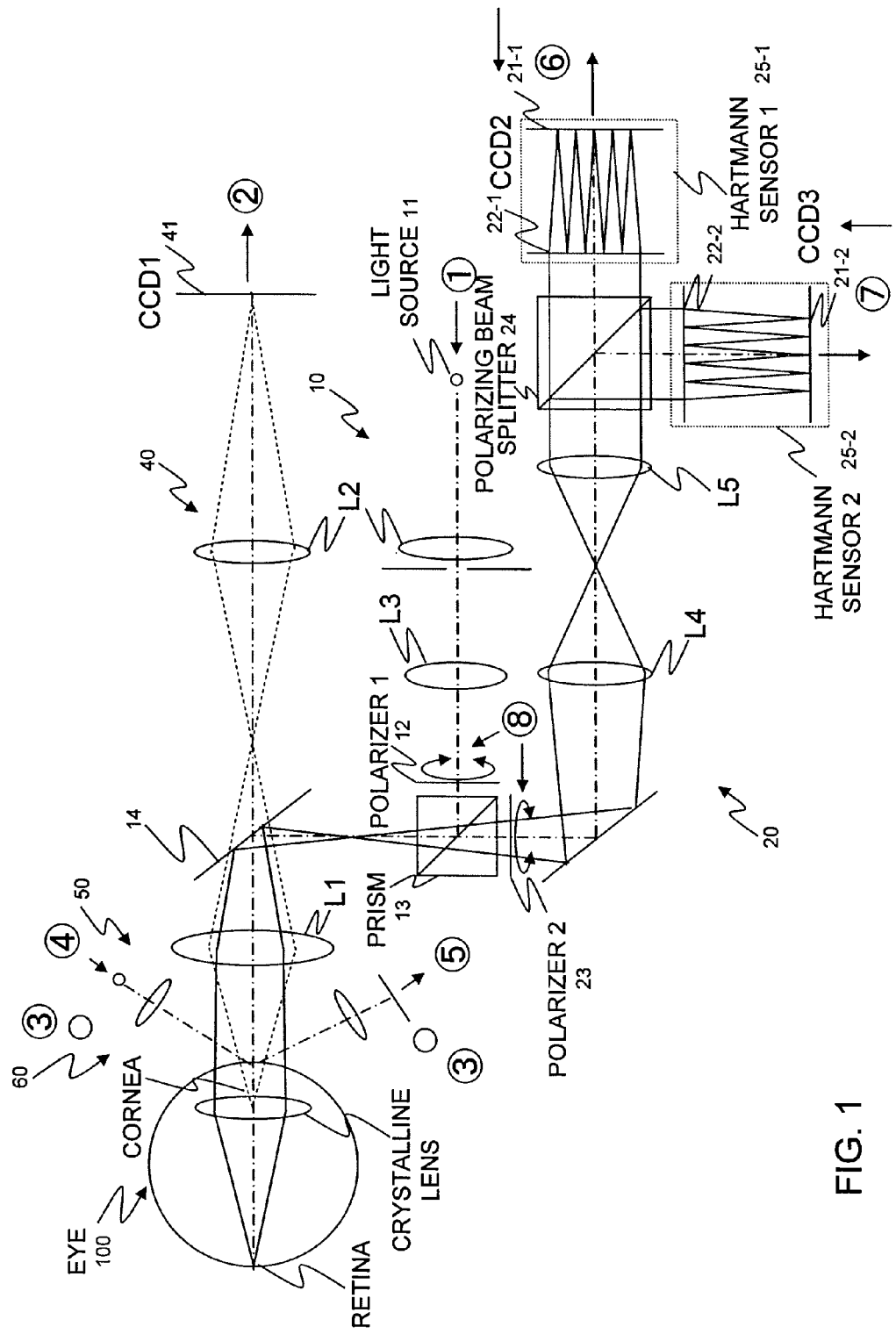
FIG. 1 is an optical arrangement view of an ophthalmologic measuring apparatus.

FIG. 1 is an optical arrangement view of an ophthalmologic measuring apparatus.

The apparatus includes a first illuminating optical system 10, a first light source part 11, a first light receiving system 20, an anterior eye observation part 40, a first adjustment optical part 50, and an anterior eye illumination part 60. Incidentally, with respect to a subject eye 100, a cornea (anterior eye part), a crystalline lens and a retina (ocular fundus) are shown.

The first light source part 11 emits light at a specified timing, and emits a light flux of a first wavelength. It is desirable that the first light source part 11 has high spatial coherence and not high temporal coherence. Here, as an example, an SLD (super luminescence diode) is adopted, and a point light source with high brightness can be obtained. Incidentally, the first light source part 11 is not limited to the SLD, and even if both the spatial and temporal coherences are high like a laser light source, it can be used by inserting a rotation diffused plate or the like to suitably lower the temporal coherence. Then, even if both the spatial and temporal coherences are not high like an LED, if only the quantity of light is sufficient, it can be used by inserting a pinhole or the like at a position of a light source in an optical path. Besides, as the wavelength of the first light source part 11 for illumination, for example, a wavelength in an infrared range (for example, 800 nm) can be used.

The first illuminating optical system 10 includes, for example, a first polarizing optical member (polarizer 1) 12, a prism 13, a beam splitter 14, and lenses L1, L2 and L3, such as a condensing lens, a cylinder lens and/or a relay lens. The first illuminating optical system 10 is for illuminating a minute area on the ocular fundus of the subject eye 100 with the light flux from the first light source part 11. The first illuminating optical system 10 illuminates the pulse light from the first light source part 11 to the ocular fundus of the subject eye 100 through the first polarizing optical member 12. The first polarizing optical member 12 alternately changes polarization conditions to a first polarized light or a second polarized light. The first and the second polarized lights are, for example, a P-polarized light and an S-polarized light or vice versa. The beam splitter 14 includes a dichroic mirror to reflect, for example, a light flux of a first wavelength and to allow a light flux of a second wavelength to pass through. The first polarizing optical member 12 is constructed such that a polarizing plate is rotatable around an optical axis.

With respect to the incident light on the subject eye 100 from the first light source part 11, the aperture stop is decentered so that the incident position of the light flux is changed in a direction perpendicular to the optical axis, the apex reflection of the lens and the cornea is prevented, and the noise can be suppressed. The aperture stop is such that its diameter is smaller than the effective range of a Hartmann plate of a first and a second conversion members 22-1 and 22-2, and the aberration of the eye influences only the light receiving side, that is, so-called single path aberration measurement is established.

Incidentally, after the incident light beam emitted from the first light source part 11 comes to have an optical path common to a measurement light beam diffusion reflected from the ocular fundus, it advances paraxially in the same way as the measurement light beam diffusion reflected from the ocular fundus. However, in the single path measurement, the diameters of the respective light beams are different, and the beam diameter of the incident light beam is set to be considerably thin as compared with the measurement light beam. Specifically, the beam diameter of the incident light beam is, for example, about 1 mm at the pupil position of the subject eye 100, and the beam diameter of the measurement light beam becomes about 7 mm. Incidentally, double path measurement can also be performed by suitably arranging the optical system.

The first light reception system 20 includes a Shack-Hartmann wavefront sensor 1_25-1, a Shack-Hartmann wavefront sensor 2_25-2, a second polarizing optical member (polarizer 2) 23, a polarizing beam splitter 24, and lenses L4 and L5. The first light receiving optical system 20 is for receiving, for example, the light flux reflected and returned from the retina of the subject eye 100, and for guiding it to the first light receiving part 21-1 and the second light receiving part 21-2. The second polarizing optical member 23 selects each polarized light component of the reflected light from the subject eye 100 illuminated according to the polarization condition of the first polarizing optical member 12. The first light receiving part 21-1 and the second light receiving part 21-2 alternately receive the reflected light of the selected polarized light component. The polarizing beam splitter 24 guides the first polarized light to the first light receiving part 21-1, and guides the second polarized light to the second light receiving part 21-2. The second polarizing optical member 23 is constructed such that the polarizing plate is rotatable around the optical axis. The first and the second polarized lights are respectively, for example, the P-polarized light and the S-polarized light or vice versa.

The Shack-Hartmann wavefront sensor 1_25-1 includes, for example, a first light receiving part 21-1 made of a CCD2 and the first conversion member 22-1 (for example, Hartmann plate). The first conversion member 22-1 is a wavefront conversion member having a lens part for converting the reflected light flux into at least 17 plural beams. As the first conversion member 22-1, plural micro-Fresnel lenses arranged on the plane perpendicular to the optical axis can be used. The reflected light from the ocular fundus is condensed on the first light receiving part 21-1 through the first conversion member 22-1. The first light receiving part 21-1 receives the light from the polarizing beam splitter 24, which has passed through the first conversion member 22-1, and generates a first signal.

The Shack-Hartmann wavefront sensor 2_25-2 includes, for example, a second light receiving part 21-2 made of a CCD3 and the second conversion member 22-2 (for example, Hartmann plate). The second conversion member 22-2 is a wavefront conversion member having a lens part for converting the reflected light flux into at least 17 plural beams. As the second conversion member 22-2, plural micro-Fresnel lenses arranged on the plane perpendicular to the optical axis can be used. The reflected light from the ocular fundus is condensed on the second light receiving part 21-2 through the second conversion member 22-2. The second light receiving part 21-2 receives the light from the polarizing beam splitter 24, which has passed through the second conversion member 22-2, and generates a second signal.

The anterior eye observation part 40 includes a third light receiving part 41 including, for example, the relay lens and the CCD1, and observes such a light flux that a pattern of the anterior eye illumination part 60, such as a Pracido ring or a Kerato ring, is reflected and returned from the anterior eye part of the subject eye 100. Incidentally, when a telecentric diaphragm is provided, the pupil diameter can be accurately measured.

The first adjusting optical system 50 is for mainly performing, for example, a working distance adjustment, and includes a light source part, a condensing lens, and a light receiving part. Here, the working distance adjustment is performed such that, for example, a parallel light flux emitted from the light source part and close to the optical axis is irradiated to the subject eye 100, and the light reflected by the subject eye 100 is received by the light receiving part through the condensing lens. Besides, in the case where the subject eye 100 is in a suitable working distance, a spot image from the light source part is formed on the optical axis of the light receiving part. On the other hand, in the case where the subject eye 100 falls outside the suitable working distance, the spot image from the light source part is formed above or below the optical axis of the light receiving part. Incidentally, since the light receiving part has only to detect a change in light flux position in a plane including the light source part, the optical axis and the light receiving part, for example, a one-dimensional CCD disposed in this plane, a position sensing device (PSD) or the like can be applied.

The anterior eye illumination part 60 includes a second light source part to emit a light flux of a second wavelength, and illuminates the anterior eye part in the specified pattern with the light flux from the second light source part by using, for example, the Pracido ring or the Kerato ring. In the case of the Kerato ring, a pattern of only the vicinity of the center of curvature of the cornea can be obtained by a Kerato image. Incidentally, the second wavelength of the light flux emitted from the second light source part can be selected to be different from, for example, the first wavelength (here, 860 nm) and to be a long wavelength (for example, 940 nm).

Although the description has been made on the assumption that the foregoing optical system has mainly the single path in which the incident light beam is thin, the invention can be applied to an ophthalmologic measuring apparatus which has a double path in which the incident light beam is thick. At that time, although the optical system is arranged in the structure for the double path, a measurement/calculation processing by an arithmetic part is the same.

(Conjugated Relation)

The ocular fundus of the subject eye 100, the first light source part 11, and the first and the second light receiving parts 21-1 and 21-2 are conjugated to each other. Besides, the pupil (iris) of the subject eye 100, the first conversion member 22-1, the second conversion member 22-2, and the diaphragm of the first illumination system 10 at the measurement light incident side are conjugated to each other.

1.2 Electrical System

Figure 2:
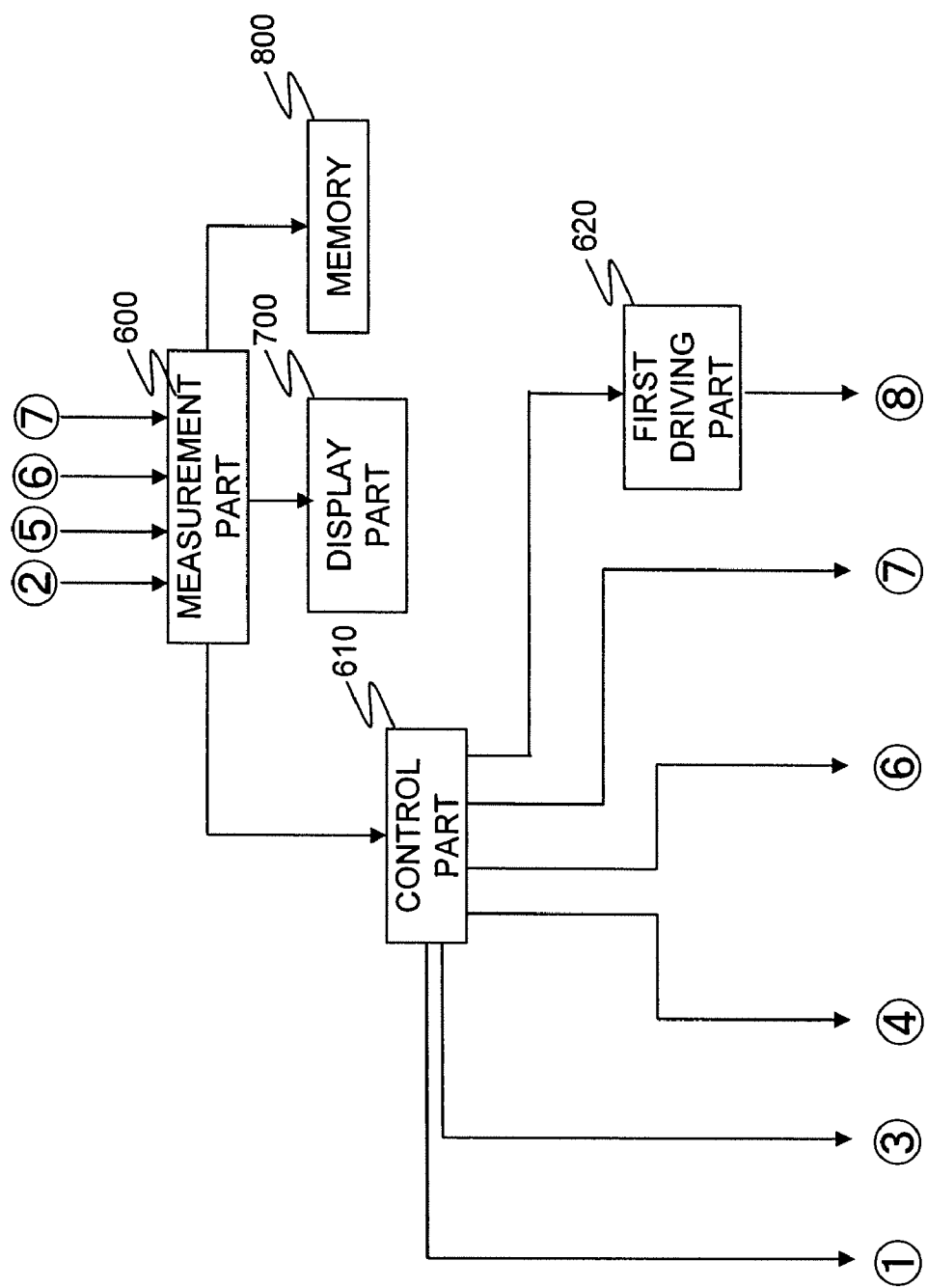
FIG. 2 is a block diagram of the ophthalmologic measuring apparatus.

FIG. 2 is a block diagram of the ophthalmologic measuring apparatus.

An electrical system of the embodiment includes a measurement part 600, a control part 610, a first driving part 620, a display part 700, and a memory 800. A signal (2) from the third light receiving part 41 of the anterior eye observation part 40, a signal (6) from the first light receiving part 21-1, a signal (7) from the second light receiving part 21-2, and a signal (5) from the light receiving part of the first adjustment optical part 50 are inputted to the measurement part 600.

The measurement part 600 measures the aberration of the subject eye 100 at short intervals based on the output from the first light receiving part 21-1 and the second light receiving part 21-2. The measurement part 600 receives the signal (6) from the first light receiving part 21-1, the signal (7) from the second light receiving part 21-2, and the signal (2) from the third light receiving part 41 of the anterior eye observation part 40, and obtains the optical characteristics of the subject eye 100 based on, for example, an inclination angle of the light flux. The measurement part 600 suitably outputs the signal corresponding to the arithmetic result or other signal/data to the control part 610 for controlling the electric driving system, the display part 700, and the memory 800.

The control part 610 is for controlling, based on the control signal from the measurement part 600, the on/off of the first light source part 11, the second light source part of the anterior eye illumination part 60, and the light source of the first adjustment optical part 50, and for controlling the exposure/readout of the CCD2 and CCD3 of the first light receiving part 21-1 and the second light receiving part 21-2. Based on the signal corresponding to the arithmetic result of the measurement part 600, the control part 610 outputs the signal (1) to the first light source part 11, outputs the signal (3) to the anterior eye illumination part 60, outputs the signal (4) to the light source of the first adjustment optical part 50, outputs the signal (6) to the first light receiving part 21-1, outputs the signal (7) to the second light receiving part 21-2, and outputs the signal (8) to the first polarizing optical member 12 and the second polarizing optical member 23.

The first driving part 620 is controlled by the measurement part 600 and the control part 610, controls the polarization condition/direction of the polarizer 1 of the first polarizing optical member 12, and alternately changes the polarization condition/direction of the incident light on the subject eye 100 to the first polarized light (P-polarized light) or the second polarized light (S-polarized light). Similarly, with respect to the polarization condition/direction of the polarizer 2 of the second polarizing optical member 23, the first driving part 620 controls the polarization condition/direction according to the polarization condition/direction of the first polarizing optical member 12 so that the reflected light from the subject eye 100 passes through, and alternately changes it to the first polarized light (P-polarized light) or the second polarized light (S-polarized light).

There is also a case where the control of the polarizing direction of the polarizer 1 or 2 is executed in conformity to the capture end timing of the CCD1 or CCD2.

The display part 700 displays the result (aberration analysis, etc.) during the arithmetic processing or after the processing as a diagram, a table, data, graphics, moving image/still image, or the like. Alternatively, the result is outputted to another apparatus.

The memory 800 suitably stores various data, such as measured data, intermediate data, and calculation result data, and setting values such as a previously set exposure time t and the number P of times of measurement as the need arises. The measurement part 600 suitably reads/writes data from/into the memory 800.

2. Aberration Analysis

2.1 Outline

The object of the measurement, that is, the eye includes the retina, the crystalline lens and the cornea. An aberration due to the cornea and the crystalline lens occurs. Although the optical system will be described below, the solid line indicates the original light beam (partially drawn), which is emitted from the first light source part 11, is imaged on the retina to form a secondary light source, passes through the optical system of the eye, further passes through the optical system of the apparatus, and is guided to the Shack-Hartmann wavefront sensor 1_25-1 or 2_25-2, and whereby the measurement becomes possible. A dotted line (partially shown) indicates an imaginary light beam to indicate a pupil conjugate. L1 denotes the objective lens common to the three systems described here. The light beam from the first light source part 11 to the retina, and from the retina to the Shack-Hartmann wavefront sensors 1_25-1 and 2_25-2 are reflected by the dichroic mirror 14.

The second light source part of the anterior eye illumination part 60 illuminates the anterior eye part with a wavelength different from one used for the wavefront measurement, and this wavelength passes through the dichroic mirror 14. This is guided to the third light receiving part (CCD1) 41 through the imaging lens L2, the anterior eye image is formed on the third light receiving part (CCD1) 41, and the anterior eye observation becomes possible. In the anterior eye part, when parallel light is incident on the eye coaxially with the pupil of the human eye or the observation optical system, the reflected image (Purkinje first image) of the cornea can be seen. By this, the alignment of the eye and the apparatus in the lateral direction is enabled.

The light from the first light source 11 passes through the polarizer 1 through the condensing lens L3, and is converted into linear polarized light, and further, a component reflected by the prism is reflected by the dichroic mirror 14 and is incident on the eye. This measurement light is scattered and reflected by the retina, the light in which a partial polarization plane is rotated is reflected by the dichroic mirror 14 through the eye optical system and the objective lens L1, and is returned to the prism 13. The reflected measurement light from the retina passes through the prism 13, passes through the polarizer 2_23 directed in a direction perpendicular to the polarizer 1_12, finally passes through the polarizing beam splitter 24, and is incident on the Shack-Hartmann wavefront sensor 1_25-1. It is assumed that the measurement part 600 performs control through the control part 610, so that both the polarizer 1_12 and the polarizer 2_23 are rotated by 90 degrees with respect to the optical axis. Then, although everything occurs similarly, the measurement light is finally reflected by the polarizing beam splitter 24. Thus, the measurement light is incident on the Shack-Hartmann wavefront sensor 2_25-2.

Although not described until here, the prism is made the beam splitter irrelevant to polarization. It may be a reflecting mirror. However, when the arrangement is made so that a center part of the light from the first light source part 11, for example, a portion (the prism can be made completely conjugate to the pupil of the eye) corresponding to a diameter of 1 mm (on the pupil of the eye) is reflected, and the measurement light passes through the other portion, effective wavefront measurement becomes possible. Although the center part can not be measured, it is especially effective as the wavefront sensor of a compensation optical system requiring high-speed measurement. For example, in a combination with a compensation optical system in which a doughnut type reflection part is provided in an imaging system of an ocular fundus image, and a high-resolution ocular fundus image is obtained by using only the outside light on the pupil, this wavefront sensor is effective.

Figure 3A:
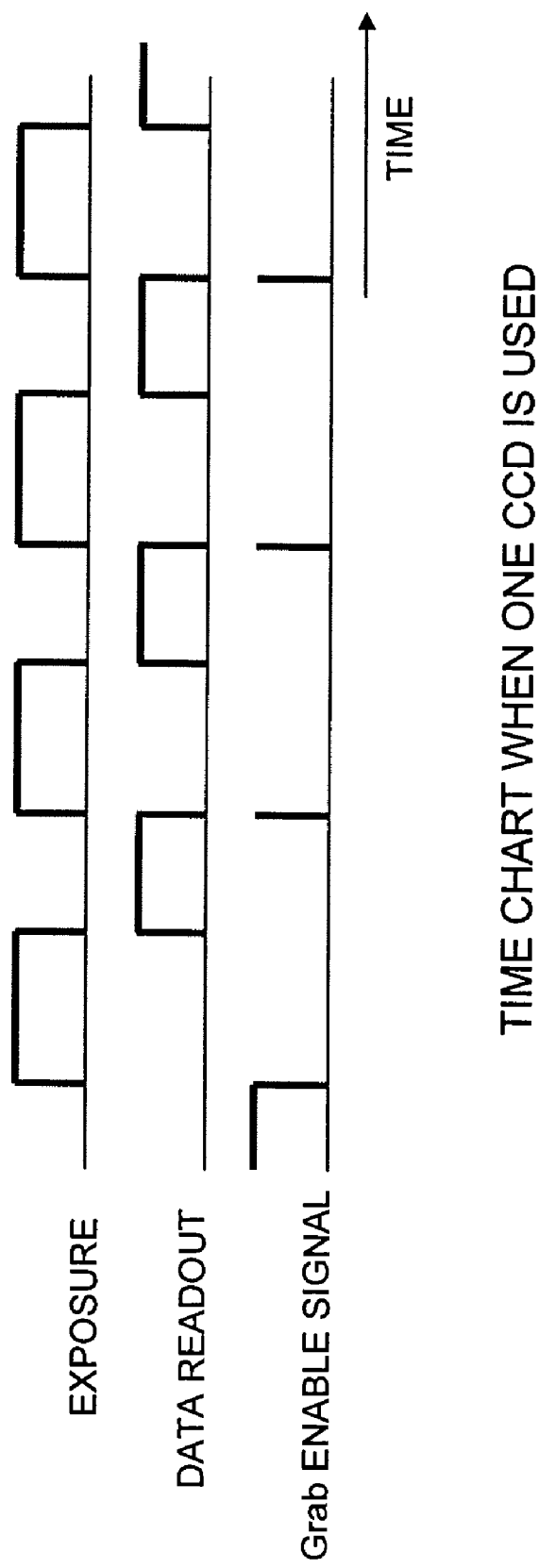
FIGS. 3A and 3B are explanatory views of time charts when one CCD is used and two CCD are used.
Figure 3B:
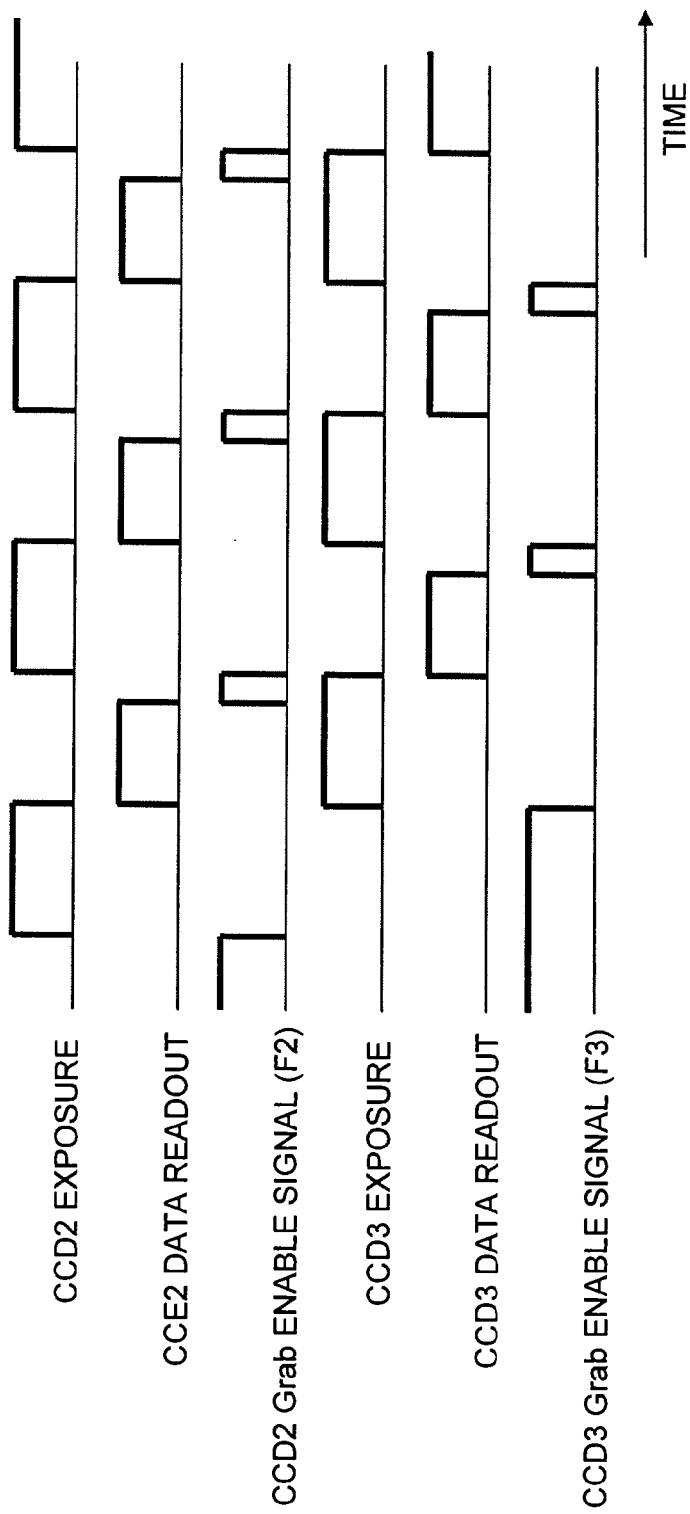

FIGS. 3A and 3B are explanatory views of time charts when one CCD is used and two CCDs are used. FIG. 3A is an explanatory view of a time chart when one CCD is used, and FIG. 3B is an explanatory view of a time chart when two CCDs are used.

The measurement part 600 reads data from the second light reception part 21-2 while the first light receiving part 21-1 is being exposed to light, and on the other hand, the measurement part reads data from the first light receiving part 21-1 while the second light receiving part 21-2 is being exposed to light. For example, as shown in FIG. 3B, while the first light receiving part (CCD2) 21-1 is being exposed to light, the measurement part 600 reads data of the second light receiving part (CCD3) 21-2 and transmits a signal (called a Grab enable signal in this example) to start exposure of the second light receiving part (CCD3) 21-2 to the control part 610. Similarly, while the second light receiving part (CCD3) 21-2 is being exposed to light, the measurement part 600 reads data of the first light receiving part (CCD2) 21-1 and transmits a Grab enable signal to start exposure of the first light receiving part (CCD2) 21-1 to the control part 610.

Incidentally, in the following description of the embodiment, the Grab enable signal is made, as an example, 1: standby state or 0: operation state.

2.2 Flowchart

Figure 4:
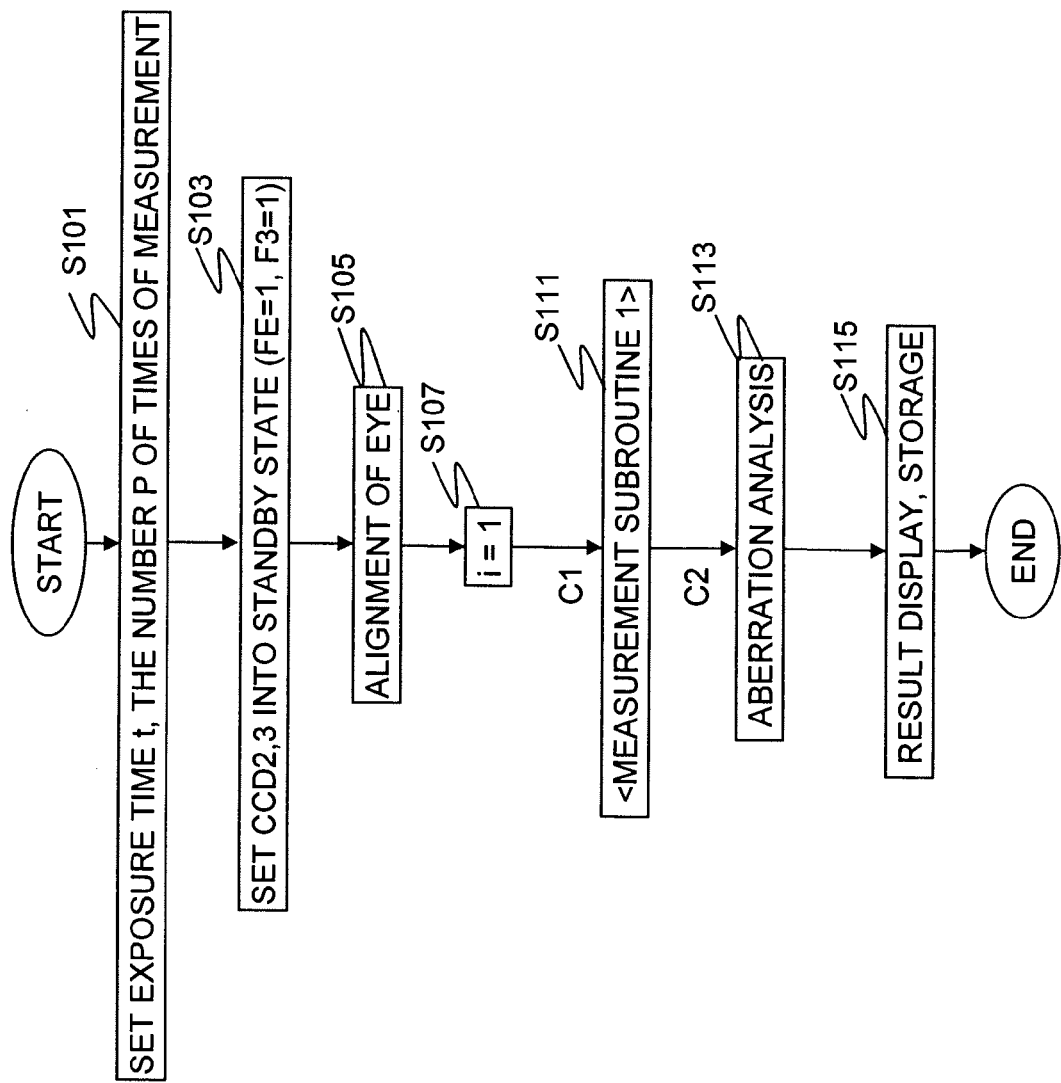
FIG. 4 is a flowchart of a whole.

FIG. 4 is the whole flowchart.

First, the measurement part 600 sets an exposure time t, and the number P of times of measurement. Incidentally, the exposure time t and the number P of times of measurement may be suitably inputted from the display part 700, or are previously stored in the memory 800 and may be read when necessary (step S101). Next, the measurement part 600 places the first light receiving part (CCD2) 21-1 and the second light receiving part (CCD3) 21-2 into a standby state (step S103). For example, the measurement part 600 sets the Grab enable signal to F2=1 and F3=1, and places, by the control part 610, the first light receiving part (CCD2) 21-1 and the second light receiving part (CCD3) 21-2 into the standby state.

Next, the measurement part 600 performs the alignment of the eye by the anterior eye image and the like obtained on the third light receiving part (CCD1) 41 (step S105). Next, the measurement part 600 sets the measured number of times to an initial value (for example, i=1) (step S107). Next, the measurement part 600 reads the data from the second light receiving part 21-2 while the first light receiving part 21-1 is being exposed to light, and on the other hand, the measurement part reads the data from the first light receiving part 21-1 while the second light receiving part 21-2 is being exposed to light, and in this way, the wavefront measurement of the subject eye 100 is executed using the two CCDs (<measurement subroutine 1>) (step S111). The details of the measurement subroutine 1 will be described later in detail. After the number of times of measurement has reached the set value, the measurement part 600 reads the measurement data from the memory 800, and performs an aberration analysis based thereon (step S113). The measurement part 600 reads the obtained analysis result of the wavefront aberration from the memory (storage part) 800, and performs, based on the analysis result, a processing for suitably displaying, for example, an ocular aberration data map, a cornea aberration data map, a bird's eye view, numerical value data, Zernike coefficient/ polynomial and the like, displays the result on the display part 700, and stores them into the memory 800 (step S115).

Figure 5:
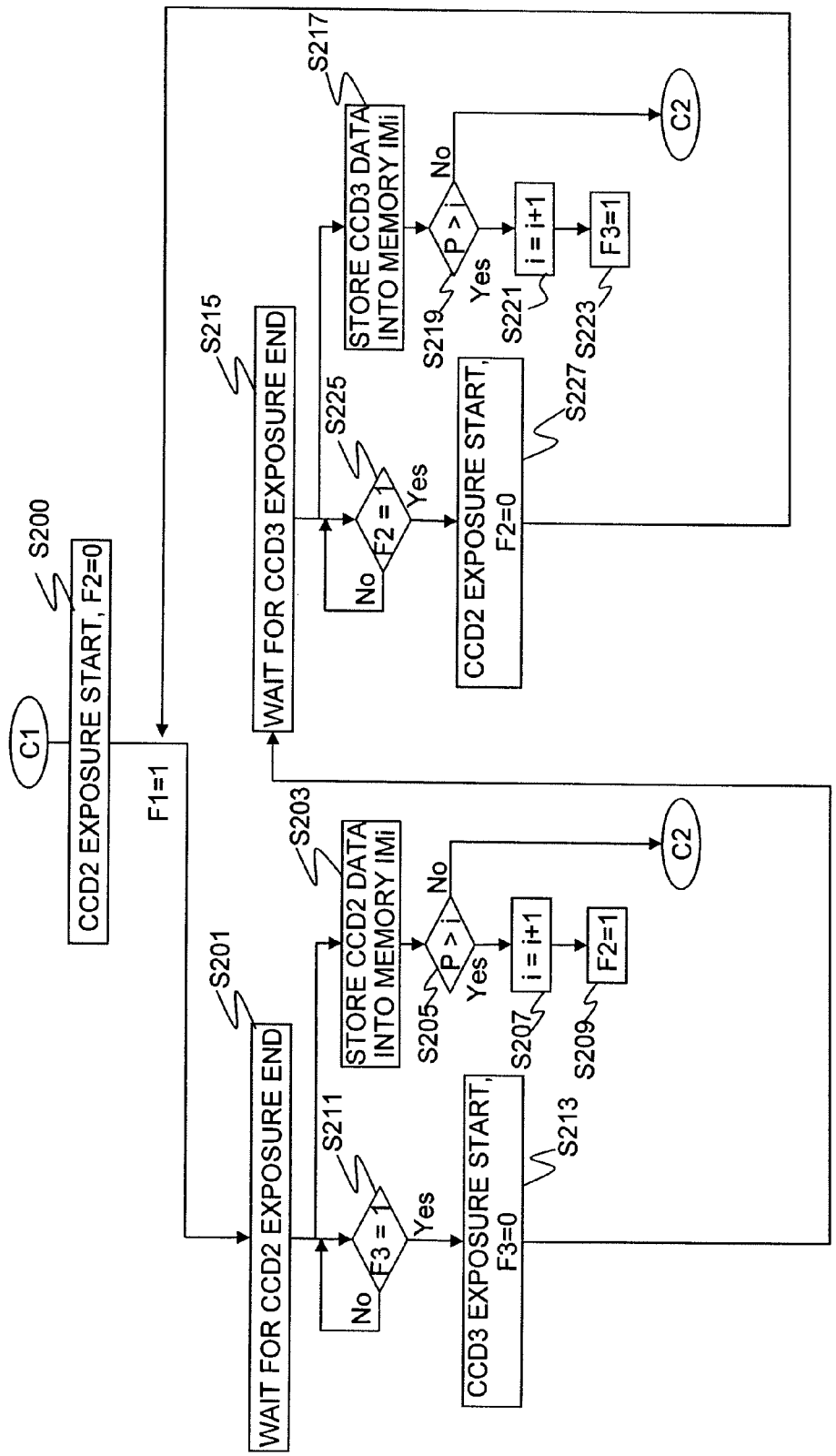
FIG. 5 is a flowchart of a measurement subroutine 1.

FIG. 5 is a flowchart of the measurement subroutine 1.

The measurement part 600 starts the exposure of the first light receiving part (CCD2) 21-1 (step S200). For that purpose, the measurement part 600 sets, for example, the Grab enable signal to F2=0, and starts the exposure of the first light receiving part (CCD2) 21-1 by the control part 610. The measurement part 600 waits for the exposure end of the first light receiving part (CCD2) 21-1 (step S201).

When the exposure is ended at step S201, the measurement part 600 reads the data of the first light receiving part (CCD2) 21-1, and stores it as data IMi corresponding to the number i of times of measurement into the memory 800 (step S203). Incidentally, at this time, identification information of the CCD2 may be stored correspondingly to the data IMi. Next, the measurement part 600 judges whether or not the measurement is performed P times or more (step S205). The measurement part 600 increments the value of i (i=i+1) in the case where the measurement is not ended (step S207), and places the first light receiving part (CCD2) 21-1 into the standby state (F2=1) by the control part 610 (step S209). Besides, when the exposure is ended at step S201, during the data read processing of the first light receiving part (CCD2) 21-1 (step S201 to S209), the measurement part 600 judges whether or not the state of the second light receiving part (CCD3) 21-2 is the standby state (F3=1) (step S211), and when it is not the standby state, the judgment is repeated until the standby state occurs.

When the second light receiving part (CCD3) 21-2 is in the standby state, the measurement part 600 starts the exposure of the second light receiving part (CCD3) 21-2 (step S213). For that purpose, the measurement part 600 sets, for example, the Grab enable signal to F3=0, and starts the exposure of the second light receiving part (CCD3) 21-2 by the control part 610. The measurement part 600 waits for the exposure end of the second light receiving part (CCD3) 21-2 (step S215). When the exposure is ended at step S215, the measurement part 600 reads the data of the second light receiving part (CCD3) 21-2, and stores it as data IMi corresponding to the number i of times of measurement into the memory 800 (step S217). Incidentally, at this time, identification information of the CCD3 may be stored correspondingly to the data IMi. Next, the measurement part 600 judges whether or not the measurement is performed P times or more (step S219). The measurement part 600 increments the value of i (i=i+1) in the case where the measurement is not ended (step S221), and places the second light receiving part (CCD3) 21-2 into the standby state (F3=1) by the control part 610 (step S223).

Besides, when the exposure is ended at step S215, in parallel to the processing (step S217 to S223) of the second light receiving part (CCD3) 21-2, the measurement part 600 judges whether or not the state of the first light receiving part (CCD2) 21-1 is the standby state (F2=1) (step S225), and when it is not the standby state, the judgment is repeated until the standby state occurs.

When the first light receiving part (CCD2) 21-1 is in the standby state, the measurement part 600 starts the exposure of the first light receiving part (CCD2) 21-1 (step S227). For that purpose, the measurement part 600 sets, for example, the Grab enable signal to F2=0, and starts the exposure of the second light receiving part (CCD2) 21-1 by the control part 610.

As described above, the measurement part 600 repeatedly performs the processing of data acquisition P times of the number of times of measurement, and when the measurements of the specified number P of times of measurement are ended at step S205 or S209, the processing of the measurement subroutine 1 is ended (C2).

2.3 Analysis of Wavefront Aberration (Zernike Analysis and RMS)

Hereinafter, the details of a method of obtaining a wavefront aberration by the Shack-Hartmann wavefront sensor will be described.

Figure 8:
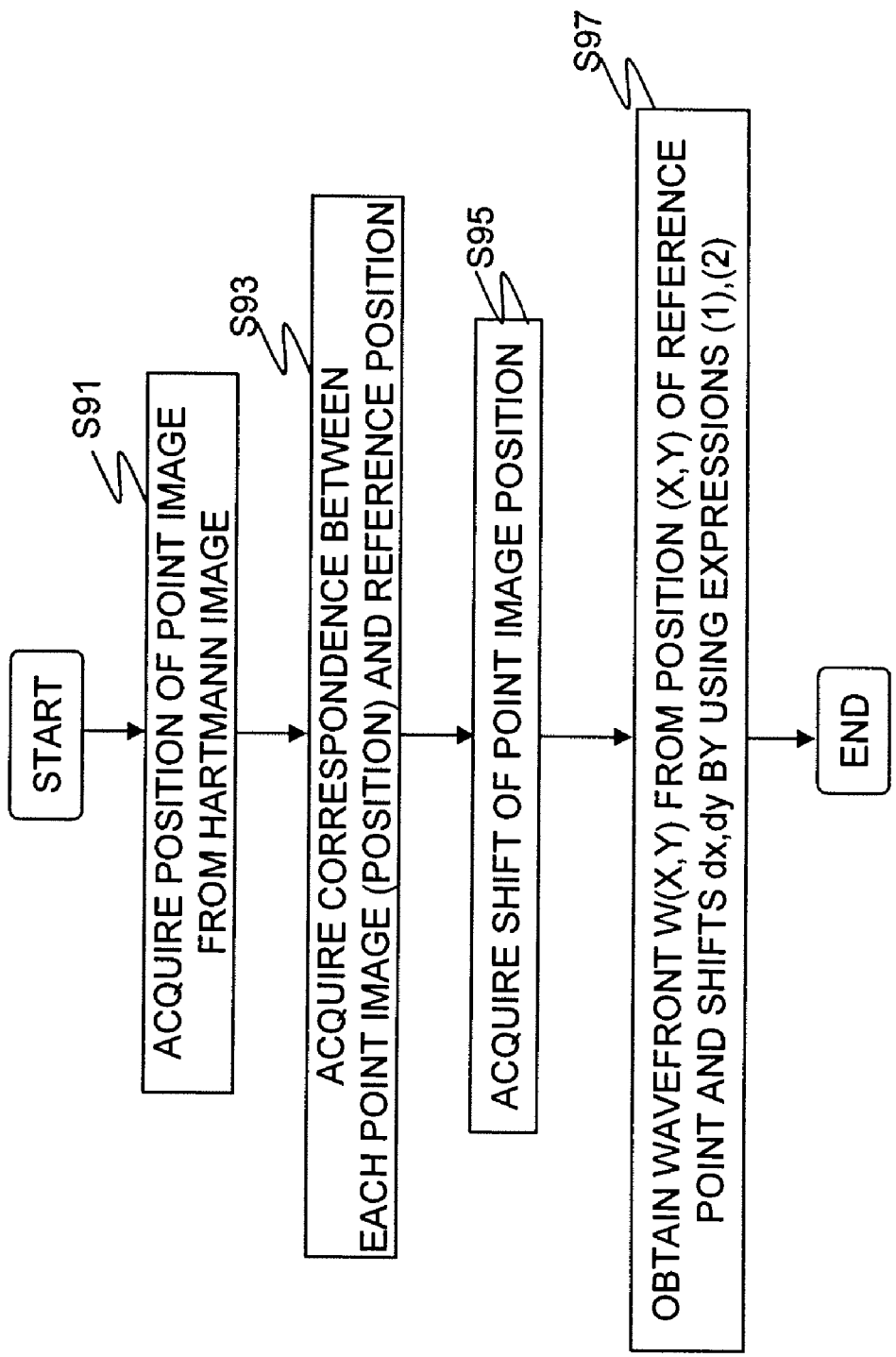
FIG. 8 is a flowchart for obtaining a wavefront.

FIG. 8 is a flowchart for obtaining the wavefront.

The measurement part 600 obtains a position of a point image from a Hartmann image (step S91). The measurement part 600 reads respective point images (positions) from the memory 800, and obtains correspondence of a reference position (step S93). Next, the measurement part 600 obtains shifts $\Delta x$ and $\Delta y$ of the point image position from the correspondence between the point image position and the reference position (step S95). Next, the measurement part 600 obtains a wavefront W(X, Y) from the position (X, Y) of the reference point and the shifts $\Delta x$ and $\Delta y$ as described below, and analyzes the wavefront aberration (step S97).

Next, the analysis of the wavefront aberration will be described. A method of calculating a Zernike coefficient $c_i^{2j-i}$ from a generally known Zernike polynomial will be described. The Zernike coefficient $c_i^{2j-i}$ is an important parameter for grasping the optical characteristics of the subject eye 100 based on the inclination angle of the light flux obtained by the CCD through the Hartmann plate by, for example, the respective light receiving parts (Hartmann sensors).

The wavefront aberration W(X, Y) of the subject eye 100 is expressed using the Zernike coefficient $C_i^{2j-i}$ and the Zernike polynomial $Z_i^{2j-i}$ by the following expression.

$$W(X, Y) = \sum_{i=0}^{n} \sum_{j=0}^{i} c_i^{2j-i} Z_i^{2j-i}(X, Y) \quad \text{[Mathematical expression 1]}$$

Where, (X, Y) denotes the horizontal and vertical coordinates of the Hartmann plate.

Besides, with respect to the wavefront aberration W(X, Y), when the horizontal and vertical coordinates of the CCD is (x, y), the distance (focal distance of the microlens of the Hartmann plate) between the Hartmann plate and the CCD is f, and the movement distance of the point image received by the CCD is ($\Delta x$, $\Delta y$), the relation of the following expression is established.

$$\frac{\partial W(X, Y)}{\partial X} = \frac{\Delta x}{f}, \quad \frac{\partial W(X, Y)}{\partial Y} = \frac{\Delta y}{f} \quad \text{[Mathematical expression 2]}$$

Where, the Zernike polynomial $Z_i^{2j-i}$ is expressed by the following expression.

Specifically, FIG. 9 is a view of the Zernike polynomial of (r, t) coordinates, and FIG. 10 is a view of the Zernike polynomial of (x, y) coordinates.

$$Z_n^m = R_n^m(r) \left\{ \begin{matrix} \sin \\ \cos \end{matrix} \right\} \{m\theta\} \quad \text{[Mathematical expression 3]}$$

$m > 0 \sin$ $m \leq 0 \cos$ $$R_n^m(r) = \sum_{S=0}^{(n-m)/2} (-1)^S \frac{(n-S)!}{S! \left\{ \frac{1}{2}(n-m)-S \right\}! \left\{ \frac{1}{2}(n+m)-S \right\}!} r^m \quad \text{[Mathematical expression 4]}$$

Incidentally, with respect to the Zernike coefficient $C_i^{2j-1}$, the specific value can be obtained by minimizing the square error expressed by the following expression.

$$S(x) = \sum_{i=1}^{\text{data number}} \left[ \left\{ \frac{\partial W(X_i, Y_i)}{\partial X} - \frac{\Delta x_i}{f} \right\}^2 + \left\{ \frac{\partial W(X_i, Y_i)}{\partial Y} - \frac{\Delta y_i}{f} \right\}^2 \right] \quad \text{[Mathematical expression 5]}$$

Where, W(X, Y): wavefront aberration, (X, Y): Hartmann plate coordinate, (Δx, Δy): movement distance of the point image received by the CCD, f: distance between the Hartmann plate and the CCD.

The arithmetic part 600 calculates the Zernike coefficient $C_i^{2j-i}$ and uses this to obtain ophthalmologic characteristics such as a spherical aberration, coma aberration, and astigmatism. The arithmetic part 600 uses the Zernike coefficient $c_i^{2j-i}$ and calculates an aberration amount $RMS_i^{2j-i}$ by the following expression.

$$RMS_i^{2j-i} = \sqrt{\frac{\varepsilon_i^{2j-i}}{2(i+1)}} c_i^{2j-i} \quad \text{[Mathematical expression 6]}$$

$$\left( \begin{matrix} \varepsilon_i^{2j-i} = 2(2j = i), \\ \varepsilon_i^{2j-i} = 1(2j \neq i) \end{matrix} \right)$$

3. Modified Example 3.1 Structure of Shifting by Half Pixel

Figure 6:
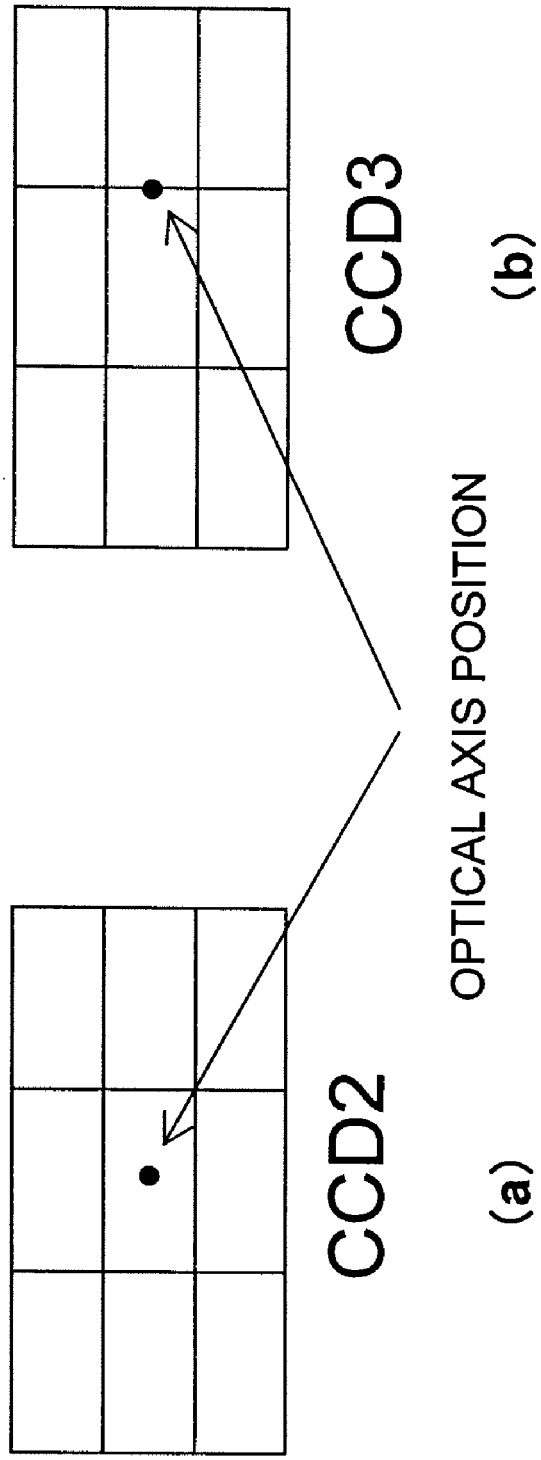
FIG. 6 is a view for explaining the arrangement of a first light receiving part (CCD2) 21-1 and a second light receiving part (CCD3) 21-2.

FIG. 6 is an explanatory view showing a structure of shifting plural light receiving parts (CCDs) by a half pixel. In an example of this drawing, the arrangement of the first light receiving part (CCD2) 21-1 and the second light receiving part (CCD3) 21-2 is shown.

The shape of one pixel of the CCD includes, for example, a square and a rectangle. In the case of the rectangle, the information amount per unit length at the long side becomes small as compared with that at the short side. Then, in this modified example, two CCDs are arranged so that they are shifted from each other in the long side direction by a half pixel. Incidentally, they may be shifted in the short side direction by a half pixel. By this, the information amount at the long side can be increased, and the measurement with high precision becomes possible. For example, when the first light receiving part (CCD2) 21-1 is arranged so that the center of the pixel at the center coincides with the optical axis, the second light receiving part (CCD3) 21-2 is arranged so that the optical axis coincides with a boundary between the pixel at the center and its adjacent pixel. Alternatively, an arrangement to the contrary may be performed.

As stated above, the first light receiving part 21-1 and the second light receiving part 21-2 are arranged to be shifted from each other by a half pixel, and based on the output from the first light receiving part 21-1 and the second light receiving part 21-2, the measurement part 600 can be constructed to perform the aberration measurement with higher precision than that based on the output of one light receiving part.

3.2 Aberration Analysis of the Apparatus

Before the measurement of the subject eye 100, the measurement part 600 may perform a calibration mode in which a not moving object, such as a model eye, is made a measurement object, and a mutual positional relation is obtained from the output of the first light receiving part 21-1 and the second light receiving part 21-2 at that time by using a transformation processing such as an affine transformation.

Hereinafter, a method of analyzing the aberration of the apparatus will be described.

First, a model eye whose aberration is known is arranged at the position of the subject eye 100. When this model eye is measured, the aberration of the optical system is added to the known aberration. From the observed point image, the aberration is calculated by an expression (previously used expression is appropriable). The amount obtained by subtracting the aberration of the model eye from that is the aberration of the apparatus. This aberration is changed into the shift of the point image, and the shifted point image is newly made the true reference point, and is used at the measurement.

Figure 7:
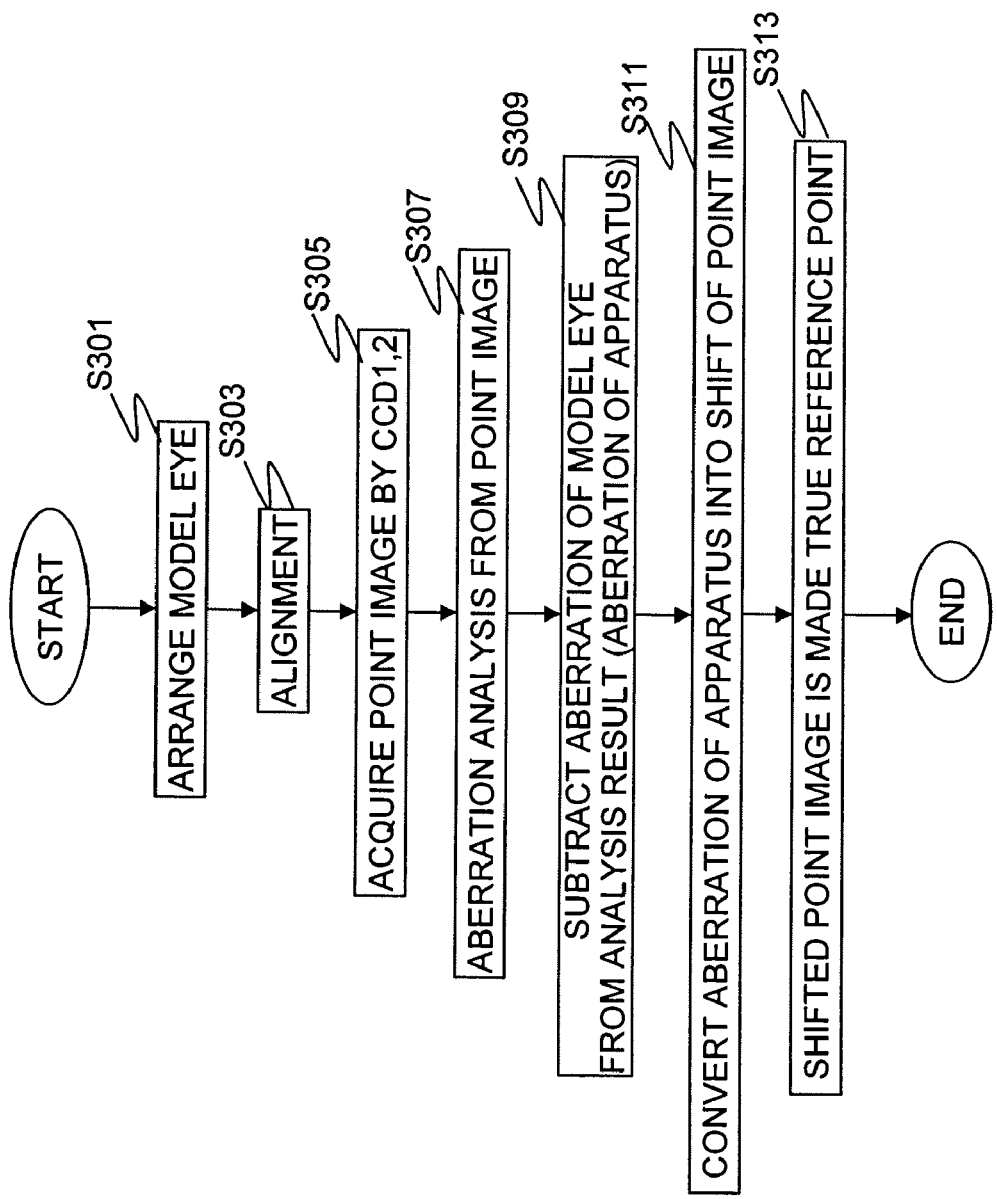
FIG. 7 is a flowchart for obtaining an aberration of an apparatus.

FIG. 7 is a flowchart to obtain the aberration of the apparatus.

The model eye whose aberration is previously known is arranged at the position of the subject eye 100 (step S301). The measurement part 600 performs alignment of the eye by the anterior eye image and the like formed on the third light receiving part (CCD1) 41 (step S303). As described in the foregoing "2.2 Flowchart", or by controlling the first driving part 620 and by wavefront measurement using a normal Hartmann plate, the measurement part 600 acquires the point image by the control part 610 and by the first light receiving part (CCD2) 21-1 and the second light receiving part (CCD3) 21-2 (step S305). The measurement part 600 performs the aberration analysis from the point image read from the first light receiving part (CCD2) 21-1 and the second light receiving part (CCD3) 21-2 (step S307). The measurement part 600 obtains the aberration of the apparatus for each of the CCD2 and CCD3 by subtracting the aberration of the model eye from the analysis result obtained at step S307 (step S309). The measurement part 600 transforms the aberration of the apparatus obtained at step S309 into a shift of the point image (step S311), regards the point image shifted correspondingly to each of the CCD2 and the CCD3 as the true reference point, and stores it into the memory 800 (step S313). The measurement part 600 obtains measurement values Δx and Δy relative to the reference point for each of the CCD2 and the CCD3, and measures, based thereon, the wavefront aberration as described in the foregoing "2.2 Flowchart".

3.3 Calibration of Arrangement Error by Affine Transformation

FIGS. 11A and 11B are explanatory views concerning the calibration of the arrangement error of a CCD of each Shack-Hartmann wavefront sensor.

FIG. 11A shows point images obtained when a stigmatic model eye is measured by a CCD, and FIG. 11B shows point images obtained by the CCD of the first light receiving part 21-1 or the second light receiving part 21-2. In FIG. 11B, it is necessary to obtain a parameter of affine transformation in each CCD. The point image positions determined from the absolute position of the reference point previously obtained through measurement are shown. Although they are not necessarily arranged in order as shown in the drawing, here, for simplification of illustration, they are shown in this way.

In general, the CCD is assembled with high precision as an optical instrument. However, there is a case where it is slightly rotated around the optical axis, the so-called tilt exists, or a position shift occurs in a plane perpendicular to the optical axis. Although this is a slight quantity, as shown in the drawing (the drawing is exaggerated), there is a case where the point images capable of being observed by each CCD at the time when the stigmatic model eye is measured are moved or distorted. For example, in FIG. 11A, there occurs only the distortion or position movement due to a lenslet array, while on the CCD of FIG. 11B, the distortion or position shift due to the CCD is added.

There is one-to-one correspondence between the point image on the CCD shown in FIG. 11A and the arrangement (reference point) of the point image, shown in FIG. 11B, at the time when the position and rotation error of the CCD do not exist, which is obtained by the previous measurement. The measurement part 600 establishes this correspondence, and approximates the relation between the arrays of two point images by the affine transformation indicated in the following expression.

$$x' = Ac_1 x + Bc_1 y + Dc_1$$

$$y' = Ac_2 x + Bc_2 y + Dc_2$$

The calibration parameters for the respective CCDs indicated below are stored in the memory (storage device) 800.
$Ac_1, Bc_1, Dc_1$
$Ac_2, Bc_2, Dc_2$ 3.4 Variation There is also conceivable a method in which a λ/4 plate is inserted in front of the objective lens, a linearly polarized light from the first light source part 11 through the first polarizing optical member (polarizer 1) 12 is once converted into a circularly polarized light, the light is reflected at a part of the retina, a circularly polarized light whose phase is inverted is made a polarized light whose polarization plane is rotated by 90 degrees from the previous one, the light passes through the second polarizing optical member (polarizer 2) 23, and the light is guided to the wavefront measurement portion. Also in this case, by the rotation of the first polarizing optical member (polarizer 1) 12 and the second polarizing optical member (polarizer 2) 23, the high-speed wavefront measurement using the two CCDs becomes possible.

3.5 Modified Example of the Illuminating Optical System and the Light Receiving Optical System In the foregoing description, the description has been given to the example in which in the illuminating optical system and the light receiving optical system, the light flux change is performed using the polarized light. However, no limitation is made to this, and another method can also be adopted. As another example, in the first illuminating optical system 10, the first polarizing optical member 12 is not provided, and in the first light receiving optical system 20, the first polarizing optical member 23 is not provided, the polarizing beam splitter 24 of the first light receiving optical system 20 is changed to a normal reflecting mirror, and is detachably/insertably provided from/to the optical path. The reflecting mirror is detachably/insertably controlled from/to the optical path according to the exposure timing to the first light receiving part and the second light receiving part by a signal from the control part 610. As a result, when the reflecting mirror is detached from the optical path, the reflected light from the ocular fundus is guided to the first light receiving part 21-1, and when the reflecting mirror is inserted to the optical path, the reflected light is guided to the second conversion member 22-2.

The invention can be widely applied to an ophthalmologic measuring apparatus, a surgery apparatus and the like.

What is claimed is:

1. An ophthalmologic measuring apparatus comprising:
    a light source part to emit a high-intensity light flux at a specified timing;
    an illuminating optical system which includes a first polarizing optical member to alternately change a polarization condition to a first polarized light or a second polarized light and illuminates the light flux from the light source part to an ocular fundus of a subject eye through the first polarizing optical member;
    a light receiving optical system which includes a second polarizing optical member to select each polarized light component of reflected light from the subject eye illuminated according to the polarization condition of the first polarizing optical member and, a first and a second light receiving parts to alternately receive the reflected light through a first and a second conversion members each dividing the reflected light of the selected polarized light component into at least 17 light fluxes; and
    a measurement part which reads first measurement data from the second light receiving part while the first light receiving part is being exposed to light, and on the other hand, reads second measurement data from the first light receiving part while the second light receiving part is being exposed to light, writes the first measurement data and the second measurement data into a memory respectively, after a number of times of measurement has reached a predetermined value, reads the first and the second measurement data from the memory and, performs an analysis of a wavefront aberration of the subject eye based on read first and second measurement data of short intervals which is shorter than intervals of measurements by each of the first and second light receiving parts.

2. The ophthalmologic measuring apparatus according to claim 1, wherein
    in the first and the second polarizing optical members, a polarizing plate is rotatable around an optical axis.

3. The ophthalmologic measuring apparatus according to claim 1, wherein
    the first and the second light receiving parts are arranged to be shifted from each other by a half pixel, and
    the measurement part performs a wavefront aberration measurement based on output from the first and the second light receiving at a higher precision than that based on output from one light receiving part.

4. The ophthalmologic measuring apparatus according to claim 1, wherein
    the measurement part performs, before measurement of the subject eye, a calibration mode in which a not moving object such as a model eye is made a measurement object, and a mutual positional relation is obtained from output of the first and the second light receiving parts at that time by using a transformation processing such as an affine transformation.

5. The ophthalmologic measuring apparatus according to claim 1, wherein
    the light receiving optical system further includes a polarizing beam splitter that guides the first polarized light to the first light receiving part, and guides the second polarized light to the second light receiving part.

6. The ophthalmologic measuring apparatus according to claim 1, further comprising a driving part that controls a polarizing direction of the first polarizing optical member, alternately changes a polarization condition/direction of the incident light of the subject eye to the first polarized light or the second polarized light, and alternately changes a polarization condition/direction of the second polarizing optical member to the first polarized light or the second polarized light according to the polarization condition/direction of the first polarizing optical member to allow the reflected light from the subject eye to pass through.

7. The ophthalmologic measuring apparatus according to claim 1, wherein
the first and the second polarized lights are a P-polarized light and an S-polarized light or vice versa.

8. The ophthalmologic measuring apparatus according to claim 1, wherein
calibration parameters are obtained from point image positions of the first and the second light receiving parts when a stigmatic model eye is measured, and stored in the memory,
the measurement part establishes a correspondence between the arrays of point images using stored calibration parameters.

* * * * *